(12) United States Patent
Digeser et al.

(10) Patent No.: US 11,839,556 B2
(45) Date of Patent: Dec. 12, 2023

(54) BONE PLATE TRIAL

(71) Applicant: Stryker European Operations Holdings LLC, Kalamazoo, MI (US)

(72) Inventors: Denis Digeser, Freiburg (DE); Nina Kozic, Bern (CH); Ulrich Spaelter, Freiburg (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 385 days.

(21) Appl. No.: 17/167,388

(22) Filed: Feb. 4, 2021

(65) Prior Publication Data

US 2021/0236304 A1 Aug. 5, 2021

Related U.S. Application Data

(62) Division of application No. 15/838,773, filed on Dec. 12, 2017, now Pat. No. 10,940,023.

(Continued)

(51) Int. Cl.
| | |
|---|---|
| *A61F 2/46* | (2006.01) |
| *A61F 2/28* | (2006.01) |
| *A61F 2/38* | (2006.01) |
| *A61B 17/80* | (2006.01) |
| *A61B 90/94* | (2016.01) |

(Continued)

(52) U.S. Cl.
CPC ........ *A61F 2/4684* (2013.01); *A61B 17/8061* (2013.01); *A61B 17/8085* (2013.01); *A61B 90/94* (2016.02); *A61F 2/2846* (2013.01); *A61F 2/389* (2013.01); *A61F 2/461* (2013.01); *A61B 17/80* (2013.01); *A61B 2090/037* (2016.02); *A61B 2090/3937* (2016.02);

(Continued)

(58) Field of Classification Search
CPC .... A61F 2/4684; A61F 2/461; A61B 17/8061; A61B 17/8085
See application file for complete search history.

(56) References Cited

U.S. PATENT DOCUMENTS

| 4,573,458 A | 3/1986 | Lower |
| 5,006,120 A | 4/1991 | Carter |

(Continued)

FOREIGN PATENT DOCUMENTS

| CA | 2179864 A1 | 12/1997 |
| WO | 2014089285 A1 | 6/2014 |

OTHER PUBLICATIONS

European Search Report and Written Opinion for EP Application No. 17207682, dated May 24, 2018.

*Primary Examiner* — Sameh R Boles
(74) *Attorney, Agent, or Firm* — Lerner David LLP

(57) ABSTRACT

Disclosed herein are a reversible bone plate template and a method for using the same to size an implant. The bone plate template may include first and second portions. The second portion may be wider than the first portion and asymmetrical about a longitudinal axis. A section between the first and second portions may allow the second portion to be moved between first and second positions such that either a first or a second surface may be a bone contacting surface. A method for sizing an implant with a bone plate template may include determining whether a first or second surface is to be placed on bone, moving a portion of the bone plate template, placing it on bone and selecting an implant based upon the bone plate template.

8 Claims, 6 Drawing Sheets

Related U.S. Application Data

(60) Provisional application No. 62/434,669, filed on Dec. 15, 2016.

(51) Int. Cl.
*A61F 2/30* (2006.01)
*A61B 90/00* (2016.01)

(52) U.S. Cl.
CPC ............. *A61B 2090/3966* (2016.02); *A61F 2002/30609* (2013.01); *A61F 2002/30616* (2013.01)

(56) References Cited

U.S. PATENT DOCUMENTS

| | | | |
|---|---|---|---|
| 5,487,741 A | 1/1996 | Maruyama et al. | |
| 5,702,470 A | 12/1997 | Menon | |
| 5,746,742 A | 5/1998 | Runciman et al. | |
| 5,906,210 A | 5/1999 | Herbert | |
| 6,059,832 A | 5/2000 | Menon | |
| 6,090,145 A | 7/2000 | Hassler et al. | |
| 6,283,969 B1 | 9/2001 | Grusin et al. | |
| 6,364,881 B1 | 4/2002 | Apgar et al. | |
| 6,436,146 B1 | 8/2002 | Hassler et al. | |
| 6,827,723 B2 | 12/2004 | Carson | |
| 6,923,817 B2 | 8/2005 | Carson et al. | |
| 7,090,676 B2 | 8/2006 | Huebner et al. | |
| 7,160,331 B2 | 1/2007 | Cooney, III et al. | |
| 7,189,237 B2 * | 3/2007 | Huebner | A61B 17/1782 606/291 |
| 7,531,003 B2 | 5/2009 | Reindel | |
| 7,547,307 B2 | 6/2009 | Carson et al. | |
| 7,572,292 B2 | 8/2009 | Crabtree et al. | |
| 7,648,508 B2 | 1/2010 | Lutz et al. | |
| 7,736,365 B2 | 6/2010 | Phillips et al. | |
| 7,963,979 B2 | 6/2011 | Phillips et al. | |
| 8,105,390 B2 | 1/2012 | Shultz et al. | |
| 8,388,689 B2 | 3/2013 | Orbay et al. | |
| 8,454,665 B2 | 6/2013 | Sidebotham | |
| 8,512,412 B2 | 8/2013 | Hanson et al. | |
| 8,545,570 B2 | 10/2013 | Crabtree et al. | |
| 8,551,180 B2 | 10/2013 | Shultz et al. | |
| 8,940,055 B2 | 1/2015 | Vanasse et al. | |
| 9,056,012 B2 | 6/2015 | Crabtree, Jr. et al. | |
| 9,173,691 B2 | 11/2015 | Orbay et al. | |
| 9,247,971 B2 | 2/2016 | Orbay et al. | |
| 9,314,342 B2 | 4/2016 | Andriacchi et al. | |
| 9,381,087 B2 | 7/2016 | Crabtree, Jr. et al. | |
| 2003/0204262 A1 | 10/2003 | Ferguson et al. | |
| 2007/0233113 A1 | 10/2007 | Kaelblein et al. | |
| 2013/0060288 A1 | 3/2013 | Rodgers et al. | |
| 2013/0204307 A1 | 8/2013 | Castaneda et al. | |
| 2013/0297033 A1 | 11/2013 | Kleinman et al. | |
| 2015/0216611 A1 | 8/2015 | Sixto et al. | |
| 2015/0313652 A1 | 11/2015 | Burckhardt et al. | |

* cited by examiner

BONE PLATE TRIAL

CROSS-REFERENCE TO RELATED APPLICATION

This application is a divisional of U.S. application Ser. No. 15/838,773, filed on Dec. 12, 2017, which claims the benefit of the filing of U.S. Provisional patent Application No. 62/434,669, filed Dec. 15, 2016, the disclosures of which are hereby incorporated herein by reference.

BACKGROUND OF THE INVENTION

The present invention relates to an apparatus and method for sizing bone implants, and in particular a reversible bone plate trial and a method for using a reversible bone plate trial for sizing purposes.

Bone plates are used in the treatment of bone fractures to hold together broken pieces of bone to allow proper healing of broken bones. Bone plates come in different configurations and have varying shapes and sizes. These configurations are specifically adapted for, inter alia, fracture location, fracture characteristics, and variations in human anatomy. Selecting the correct bone plate and determining the optimal position to affix the plate on the bone is crucial for successful treatment of bone fractures. However, determining the correct size of the bone plate to be used, as well as the position in which it is to be affixed to the bone can be challenging.

Typically, an x-ray serves as a scan of the fracture to allow the surgeon to generally select the appropriately sized bone plate, and where it should optimally be affixed to the bone. Preoperative planning, however, may not be sufficient to properly determine the correct size and positioning for a bone plate. Thus, bone plate trials are provided and allow surgeons to choose the appropriate bone plate and determine the position intraoperatively, which provides for more precise bone plate selection and positioning.

Bone plate trials themselves may come in many configurations to match fracture patterns and anatomical variations. Surgeons typically place bone plate trials against the fractured bone to test for appropriate size and positioning. A trial-and-error procedure is used whereby the surgeons tests different bone plate trials, until the correct bone plate trial is identified. This trial-and-error procedure increases the effort and duration of the surgery, especially when asymmetric bone plates configured for use on either left or right anatomical structures are required. For example, fractures of the distal radius may require specific bone plate trials that are configured for either the left or right distal radius, and consequently require multiple sets of bone plate trials—i.e., a first set for the right distal radius, and a second set for the left distal radius. This places an additional burden on the surgeon to ensure that a bone plate corresponding to the specific side of the anatomy is selected.

Contourable bone plate trials may reduce the number of trial plates required, wherein a surgeon may be able to shape the bone plate trial to align with the anatomy of the fractured bone. However, rigid contourable plate trials may require substantial force to deform them to anatomically alignment, whereas soft contourable plate trials, which may be deformed by hand, are prone to kinks and folds resulting in improper sizing. Therefore, suitable improvements in bone plate trials are required.

BRIEF SUMMARY OF THE INVENTION

Disclosed herein are bone plate templates and methods for sizing an implant with a reversible bone plate template.

In a first aspect of the present invention, a bone plate template is provided. The bone plate template may include a first surface, a second surface, a first portion, a second portion, and a section. The second surface may be opposite the first surface. The second portion may be wider than the first portion and asymmetrical about a longitudinal axis extending between the first and second portions. The section may be between the first and second portions. The section may allow the second portion to be moved to first and second positions with respect to the first portion. When the second portion is in the first position, the first surface may be a bone contacting surface, and when the second portion is in the second position, the second surface may be the bone contacting surface.

In accordance with the first aspect, the second portion may be moved to the first and second positions with respect to the first portion by deforming the section along a bending axis substantially transverse to the longitudinal axis. The bone plate template may be elastically deformed about the bending axis.

Further in accordance with the first aspect, the section may be selected from the group consisting of grooves, slots and notches.

Still further in accordance with the first aspect, the second portion may be contoured to substantially match a volar surface of a distal radius. The section may be located at a metaphyseal region of the distal radius.

Still further in accordance with the first aspect, the first position may allow for the bone plate template to be placed on a right distal radius and the second position may allow for the bone plate to be placed on a left distal radius. In the first and second positions, the second portion may be aligned with a volar tilt of the distal radius.

In other aspects, the template may further comprise a plurality of markings. The plurality of markings may be located near the first portion of the bone plate template. The plurality of markings may be selected from the group consisting of grooves, slots and notches.

A second aspect of the present invention is a method of sizing an implant. A method in accordance with this aspect of the invention may include the steps of providing a bone plate template having a first and a second surface, determining whether the first or second surfaces are to be placed on a bone, moving a second portion of the bone plate from a first position to a second position, placing the bone plate template on the bone, and selecting an implant based upon the bone plate template. The step of determining whether the first or second surfaces are to be placed on the bone may be based upon the configuration of the second portion with respect to the bone. The second portion may be moved from the first position to the second position with respect to the first position.

The method may further include the step of determining a length of the implant based upon at least one marking on the first portion. The second portion may be larger than the first portion and asymmetrical about a longitudinal axis extending between the first and second portions. The bone may be a distal radius and the placing step may include placing the bone template on a volar surface of the distal radius.

BRIEF DESCRIPTION OF THE DRAWINGS

A more complete appreciation of the subject matter of the present invention and the various advantages thereof can be realized by reference to the following detailed descriptions, in which reference is made to the accompanying drawings.

DETAILED DESCRIPTION

In describing preferred embodiments of the disclosure, reference will be made to directional nomenclature used in describing the human body. It is noted that this nomenclature is used only for convenience and that it is not intended to be limiting with respect to the scope of the invention. As used herein, when referring to bones or other parts of the body, the term "proximal" means closer to the heart and the term "distal" means more distant from the heart. The term "medial" means toward the midline of the body and term "lateral" means away from the midline of the body.

Figure 1:
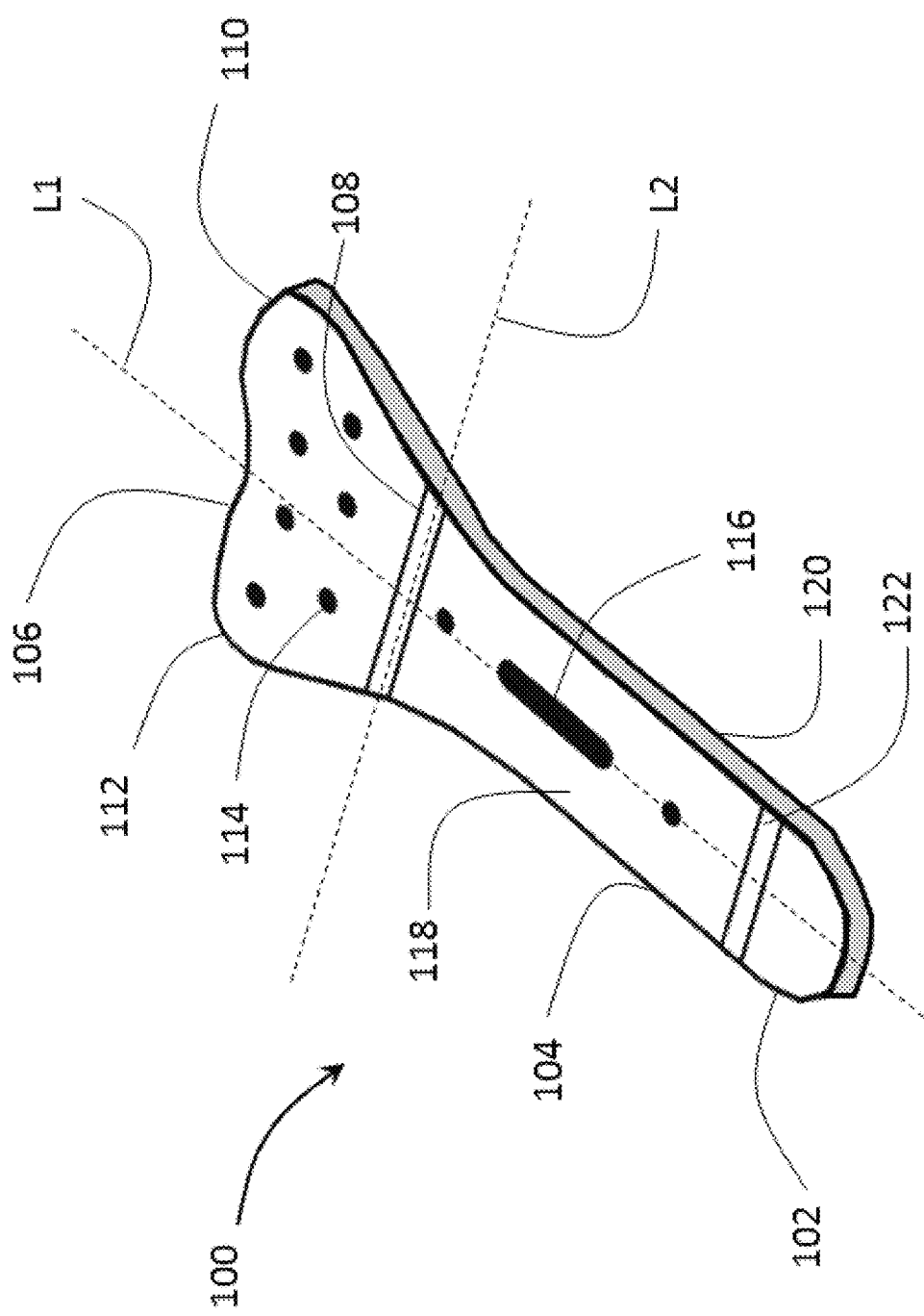
FIG. 1 is a perspective view of a bone plate trial according to one embodiment of the present invention.
Figure 2B:
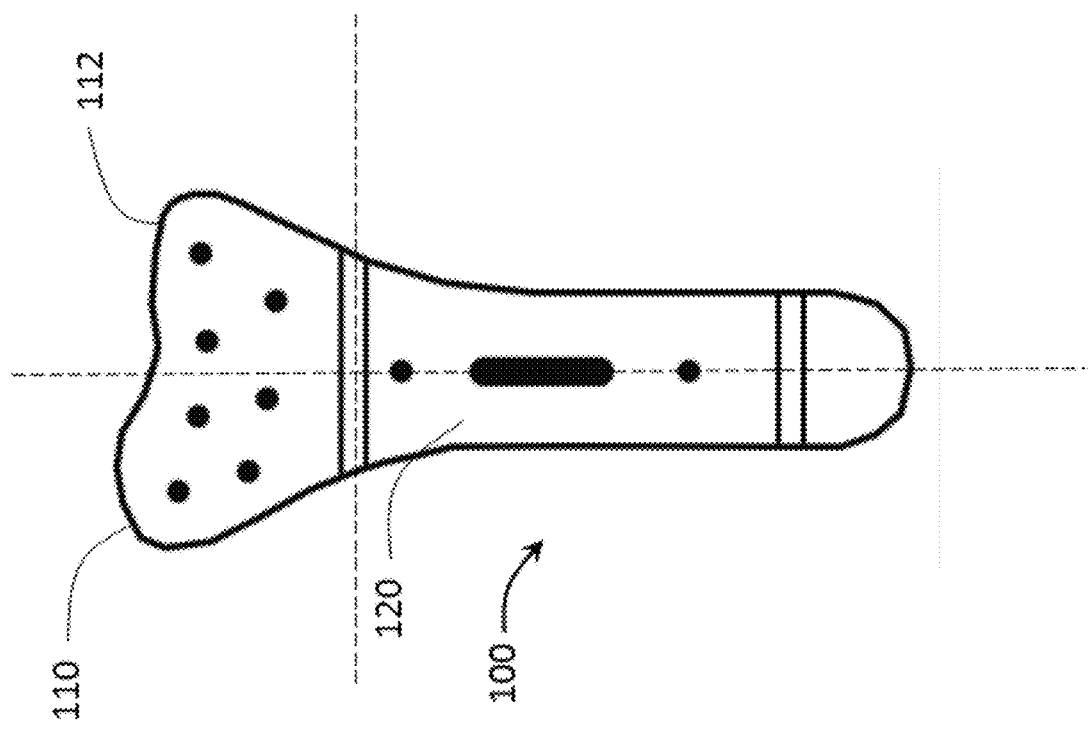
FIG. 2B is a front view of the bone plate trial of FIG. 1 in a second position.
Figure 2A:
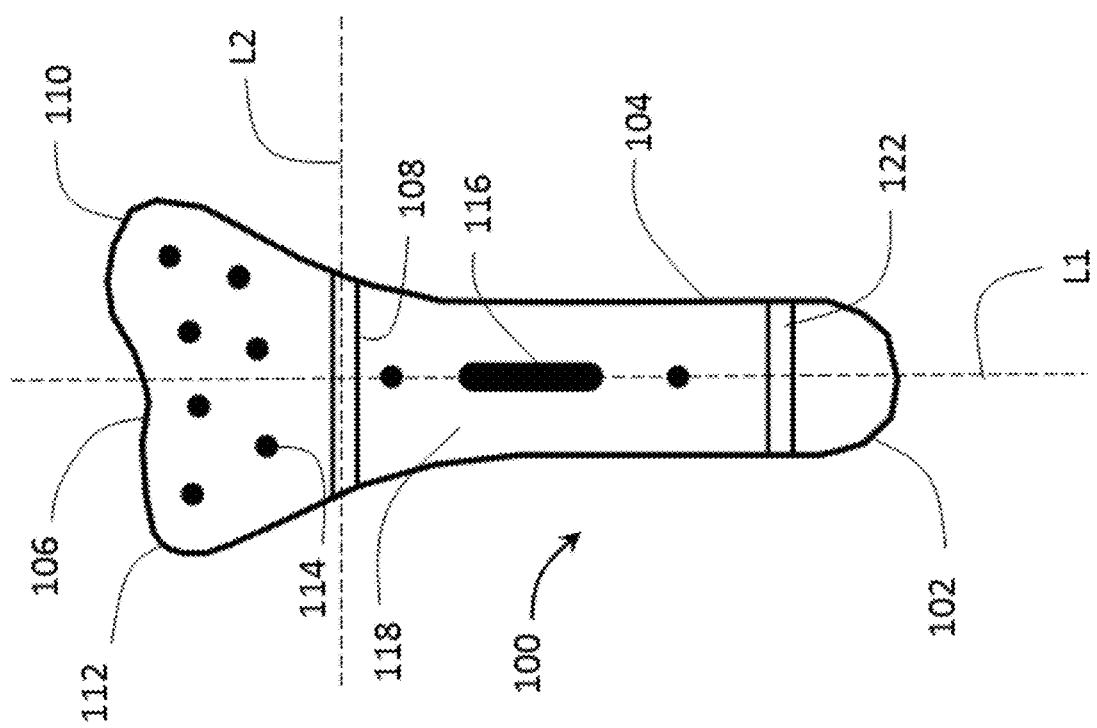
FIG. 2A is a front view of the bone plate trial of FIG. 1 in a first position.

FIG. 1 depicts a bone plate trial 100 for sizing a distal radius plate (not shown). Bone plate trial 100 includes a tail section 102, a body section 104, and a head section 106. Head section 106 comprises an ulnar-side section 110 and a radial-side section 112. As shown in FIG. 1, the profile of ulnar-side section 110 is different from the radial-side section 112, and therefore head section 106 is asymmetric about a longitudinal axis L1 extending across bone plate trial 100. In particular, ulnar-side section 110 extends more distally than radial-side section 112. One or more apertures 114 are present across head section 106. Apertures 114 allow K-wires or screws to temporarily fix bone plate trial 100 on bone. Apertures 114 shown here are circular, but other aperture configurations, such as triangular, rectangular, etc., may also be used.

A bending section 108 separates head section 106 from body section 104. The bending section allows head section 106 to be bent along an axis L2 with respect to body section 104. Bending section 108 may include of any of grooves, slots, notches, and a flexible portion as more fully explained below. Body section 104 includes additional apertures including an oblong aperture 116 as shown in FIG. 1, which may allow access for certain tools such as a drill bit or other tooling with marking capabilities. Oblong aperture 116 may also serve as openings for k-wire implantation to allow for subsequent positioning of bone plate trial 100. Markings or other indicators may also be present on body section 104 to facilitate bone plate sizing and positioning.

A band 122 is located between body section 104 and tail section 102. Band 122 may be a continuous linear slot extending transversely across bone plate trial 100 as shown in FIG. 1 and may include any of grooves, slots and notches (not shown). Band 122 may facilitate in bending tail section 102 relative to body section 104 to allow for anatomical alignment of bone plate trial 100. Band 122 may also be configured to be detachable from body 104 to create a shorter bone plate trial 100 if necessary.

Figure 3A:
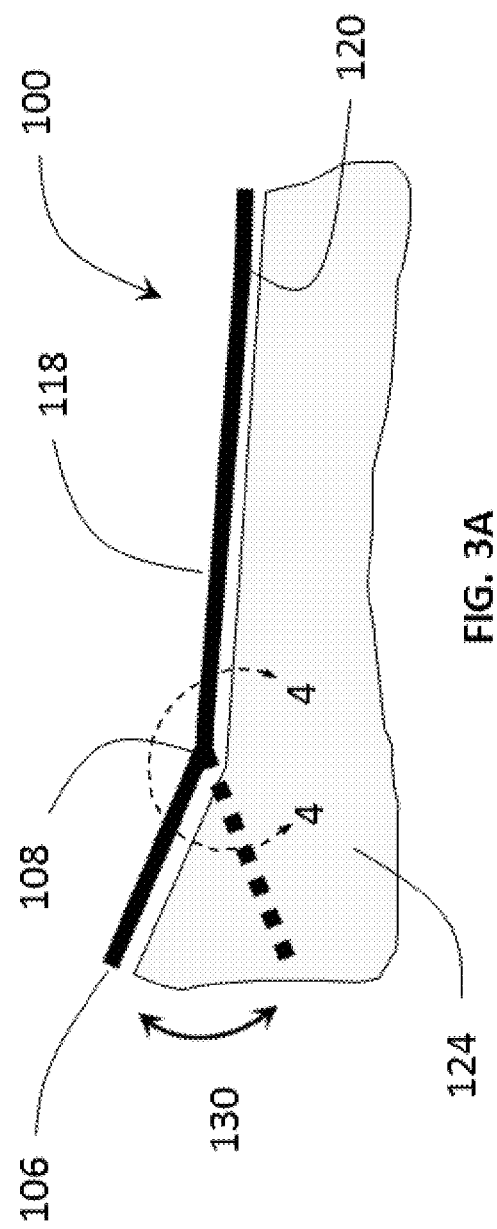
FIG. 3A is side elevation view of the bone plate trial of FIG. 1 in the first position.
Figure 3B:
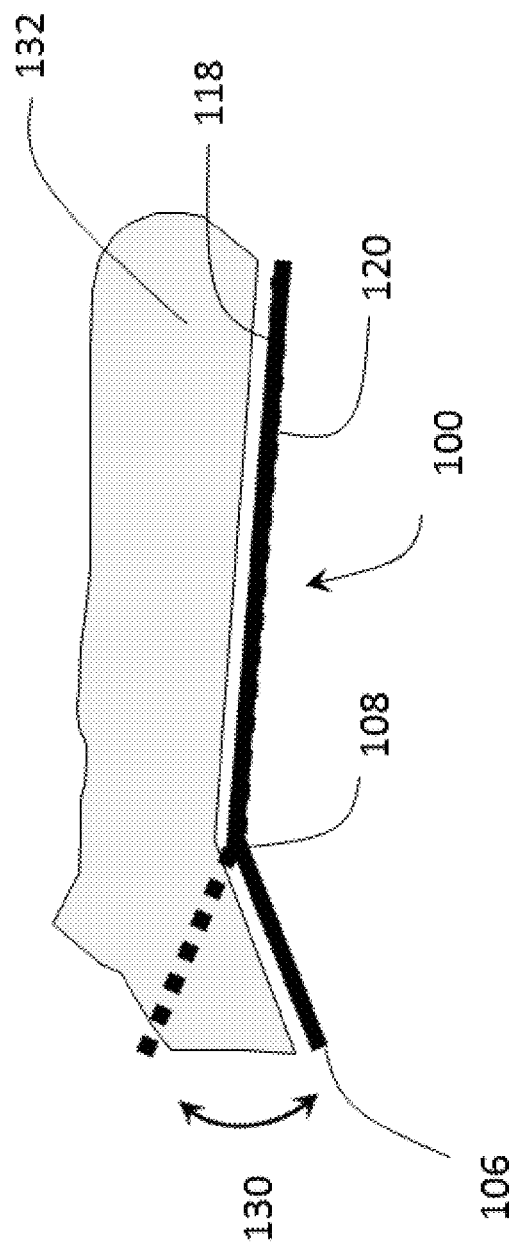
FIG. 3B is a side elevation view of the bone plate trial of FIG. 1 in the second position.

FIGS. 2A, 3A and 2B, 3B show bone plate trial 100 in a first and second position, respectively. Bone trial 100 has a first surface 118 and an opposite second surface 120. In the first position, second surface 120 is the bone contacting surface as best shown in FIG. 3A. Whereas in the second position, the first surface 118 is the bone contacting surface as best shown in FIG. 3B. The side elevation views of FIGS. 3A and 3B of bone plate trial 100 further illustrate the bending of head section 106 with respect to body section 104. In the first position shown in FIG. 3A, head section 106 is rotated along bending section 108 as indicated by rotation arrow 130 to align bone plate trial 100 with a volar tilt of a left distal radius 124.

Bone plate trial 100 can also be used for a right distal radius 132 as shown in FIG. 3B. Head section 106 is rotated along bending section 108 as indicated by rotation arrow 130 until head section 106 is aligned with the volar tilt of right distal radius 132. In this second position, first surface 108 serves as the bone contacting surface. Hence, bone plate trial 100 can be used on a left distal radius 124 (FIGS. 2A and 3A) or on a right distal radius 132 (FIGS. 2B and 3B) by reversing the bone contacting surface and rotating head section 106 to align with the respective volar tilt.

Figure 4B:
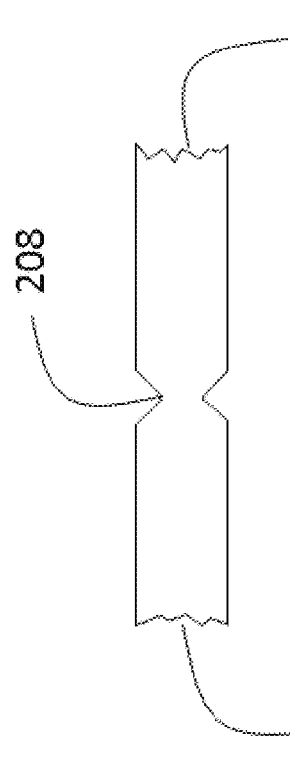
FIGS. 4A-4D are side elevation views of a bending section depicting various embodiments of the bending section.
Figure 4D:
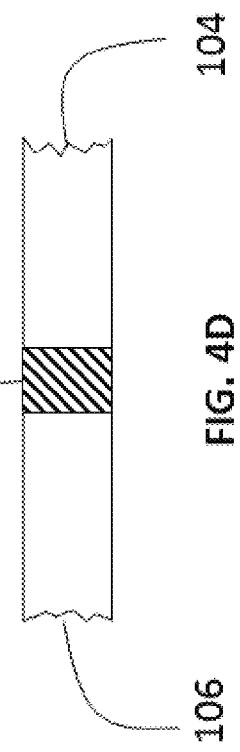
Figure 4A:
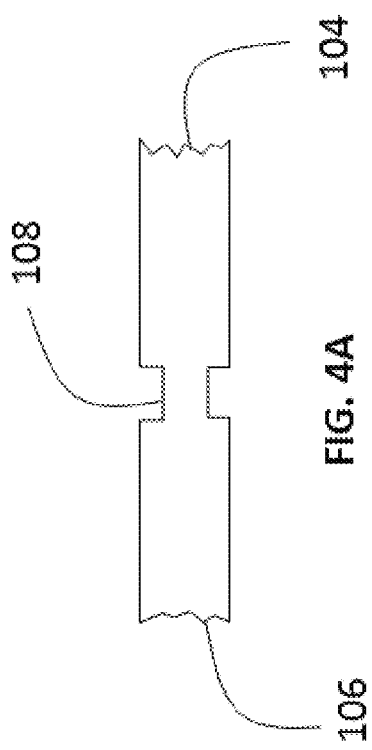
Figure 4C:
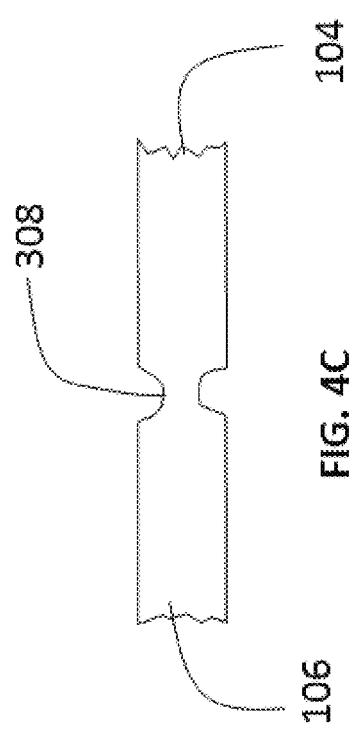

FIGS. 4A-4D show details of the bending section depicting various embodiments. The bending section may include grooves or notches such as a rectangular groove 108 (FIG. 4A), a V-shaped groove 208 (FIG. 4B), or a U-shaped groove 308 (FIG. 4C). Alternatively, the bending section may include a bending band 408. Bending band 408 may be a malleable material with a lower elastic modulus than head section 106 and body section 104, and consequently allow head section 106 to be bent with reference to body section 104.

Figure 5A:
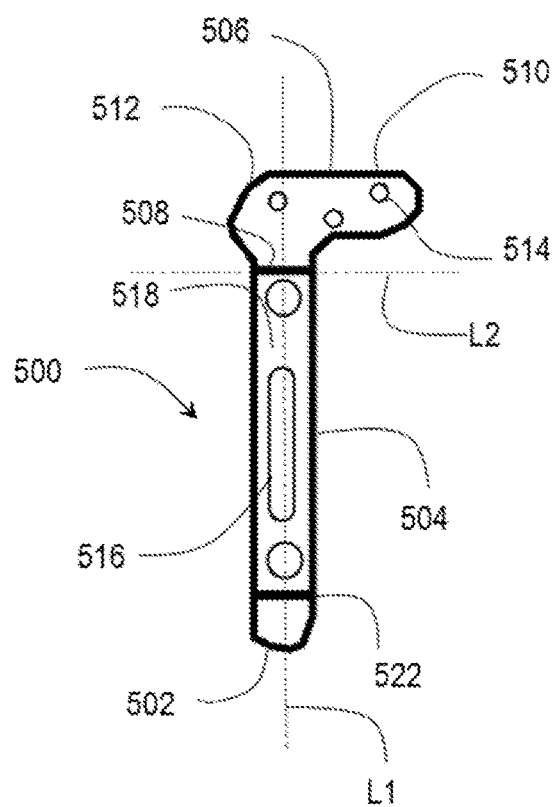
FIG. 5A is front view of a bone plate trial according to another embodiment of the present invention in a first position.
Figure 5B:
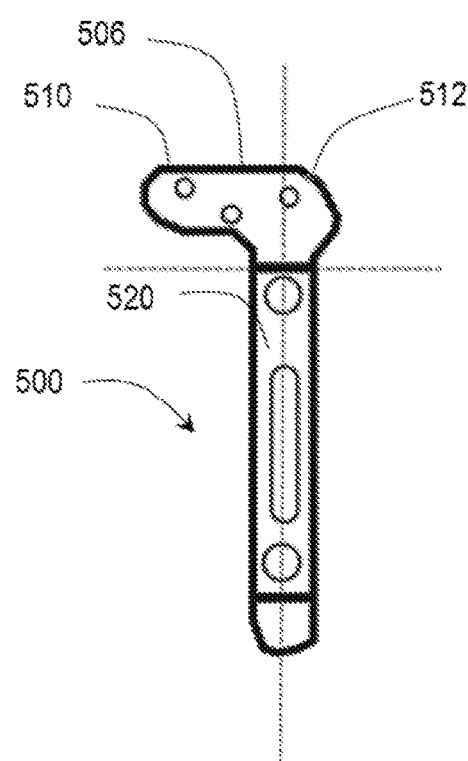
FIG. 5B is a front view of the bone plate trial of FIG. 5A in a second position.

Referring now to FIGS. 5A and 5B, there is shown another embodiment of the present invention in the form of a bone plate trial 500 for sizing a tibial bone plate. Bone plate trial 500 is similar to bone plate trial 100, and therefore like elements are referred to with similar reference numeral within the 500-series of numbers. Bone plate trial 500 is configured to be used as reversible trial for sizing tibial bone plates for either left or right tibial fractures, whereby either a first surface 518 or a second surface 520 may be the bone contacting surface. Bending sections at 508 and 522 allow bone plate trial 500 to be aligned with the left or right tibia. In a first position, second surface 520 serves as the bone contacting surface to be placed on a right tibia, and in a second position, first surface 518 serves as the bone contacting surface to be placed on a left tibia.

Figure 6:
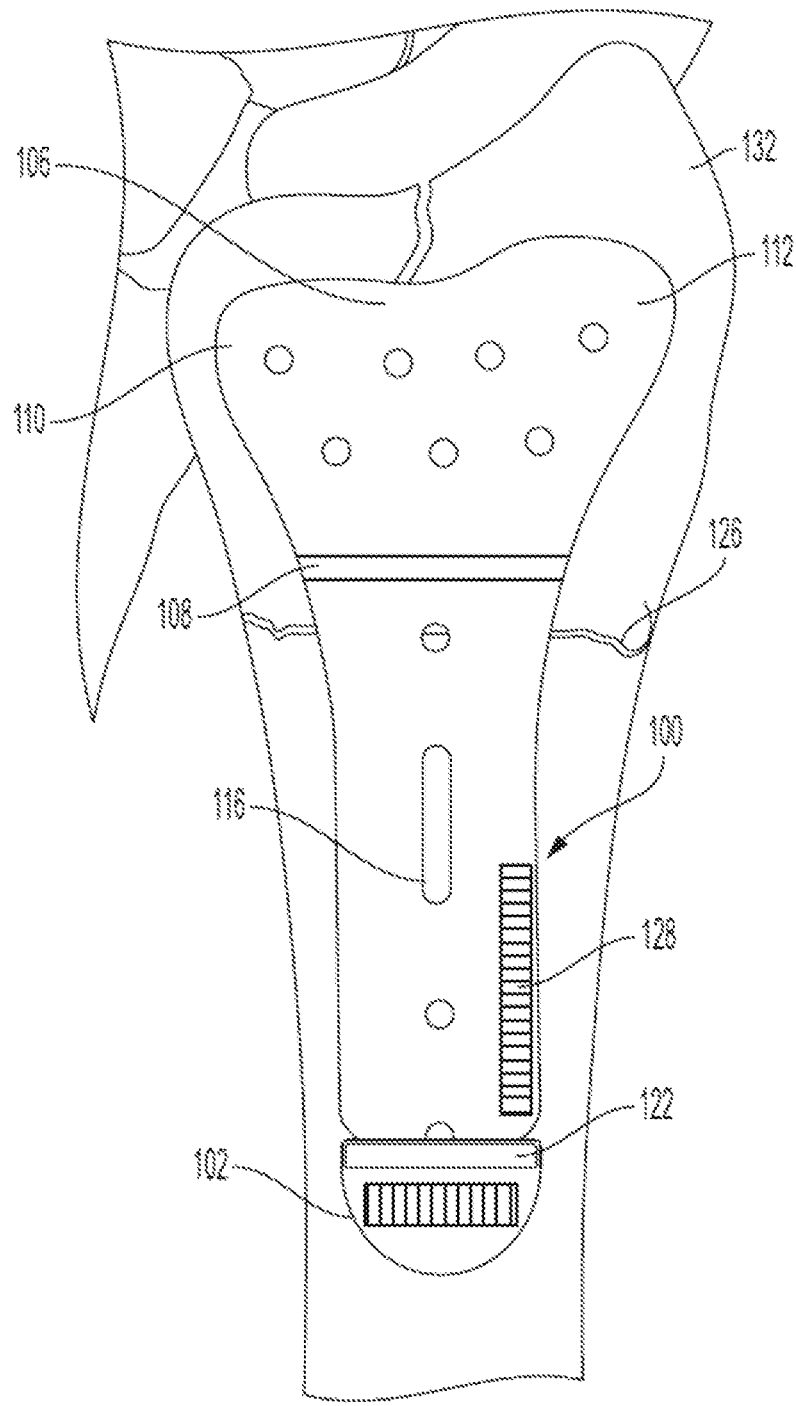
FIG. 6 is a front view of the bone plate trial of FIG. 1 placed over a bone fracture.

In a method according to a further aspect of the present invention, bone plate trial 100 is used to size a bone plate. As more fully explained above, bone plate trial 100 may be used on either a left or right distal radius. A surgeon selecting a distal radius bone plate trial to size a distal radius bone plate may only need to select a bone plate trial that covers fracture 126 as best shown in FIG. 6. Once a reversible bone plate trial 100 is selected, the surgeon may determine if first surface 118 or second surface 120 must be placed the distal radius depending on whether the fracture is on the right or left distal radius. As illustrated in this example, the surgeon may then place the selected bone plate trial on right distal radius 132 shown in FIG. 6, and bend head section 106, and tail section 102 if necessary, to align bone plate trial 100 with the volar tilt of right distal radius 132. After selected bone plate trial 100 is properly positioned on right distal radius 132, the surgeon may use apertures 114 to temporarily fix bone plate trial 100 by using K-wires or screws. Oblong aperture 116 may also be used to make temporary markings on right distal radius 132 with marking tools such as a drill bit with laser marking capability. If, after placing, the selected bone plate trial on fracture 126, the surgeon realizes that bone plate trial 100 does not optimally cover fracture area—i.e., is larger or smaller than necessary, the surgeon may simply proceed to select a larger or smaller bone plate trial as required, and repeat the same steps. Alternatively, if the selected bone plate trial is larger than required, the surgeon may remove trial section 102 by detaching it from body section 104 along band 122 to readily adjust length of bone plate trial 100 without having to select a new bone plate trial. Ultimately, a bone plate corresponding to the most suitable trial is selected and implanted. K-wires, screws or markings that were utilized or implanted/made with trial 100 can aid in this implantation.

While the present disclosure exemplifies reversible bone plate trial for distal radius and tibial fractures, bone plate trials disclosed herein may be used in treatment of a wide variety of fractures including fractures of the ulna, phalanges, humerus, femur, etc.

Bone plate trials of the present disclosure may be, but are not limited to, being made of any polymer such as polyetheretherketone ("PEEK"), polyarlyetherketones ("PAEK"), ultra-high molecular weight polyethylene ("UHMWPE"), metals such as titanium, stainless steel, aluminum, or other suitable material (e.g., ceramic) that is biocompatible and possess sufficient strength and rigidity. Bone plate trials may also include markings 128 to aid in sizing and positioning as shown in FIG. 6. Marking 128 may also denote bone contacting surface for the left or right distal radius or another anatomical feature. Radio-opaque markers may be used to facilitate sizing and positioning of the bone plate trials of the present disclosure.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A method of sizing an implant comprising the steps of: providing a bone plate template having a first and a second oppositely oriented surfaces, a first rigid portion and a second rigid portion; determining whether the first or second surfaces are to be placed on a bone based upon the configuration of the second rigid portion with respect to the bone; moving the second rigid portion from a first position to a second position with respect to the first rigid portion; placing the bone plate template on the bone; and selecting an implant based upon the bone plate template, said method further including the step of reducing the size of the bone plate template to select the implant, wherein the step of reducing the size of the bone plate template is performed by detaching a tail portion of the first rigid portion.

2. The method of claim 1, further comprising the step of determining a length of the implant based upon at least one marking on the first rigid portion.

3. The method of claim 1, wherein the second rigid portion is larger than the first rigid portion and asymmetrical about a longitudinal axis extending between the first and second rigid portions.

4. The method of claim 1, wherein the bone is a distal radius and the placing step includes placing the bone template on a volar surface of the distal radius.

5. The method of claim 1, wherein the step of moving the second rigid portion from a first position to a second position is performed by bending a first section disposed between the first and second rigid portions.

6. The method of claim 5, wherein the first section includes a first groove on the first surface.

7. The method of claim 6, wherein the first section includes a second groove on the second surface.

8. The method of claim 1, wherein the step of detaching a tail portion of the first rigid portion is performed using a detachable element extending between the tail portion and the first rigid portion.

* * * * *